United States Patent [19]

Moloy

[11] Patent Number: 4,902,833
[45] Date of Patent: Feb. 20, 1990

[54] BISPHOSPHINE DIOXIDES

[75] Inventor: Kenneth G. Moloy, Charleston, W. Va.

[73] Assignee: Union Carbide Chemicals and Plastics Company Inc., Danbury, Conn.

[21] Appl. No.: 157,716

[22] Filed: Feb. 19, 1988

[51] Int. Cl.$^4$ .............................................. C07F 9/53
[52] U.S. Cl. ...................................................... 568/14
[58] Field of Search .......................................... 568/14

[56] References Cited

U.S. PATENT DOCUMENTS

| 3,126,416 | 3/1964 | Williams | 568/14 |
|---|---|---|---|
| 3,532,774 | 10/1970 | Maier | 260/928 |
| 4,447,584 | 5/1984 | Bergeret et al. | 525/340 |
| 4,581,416 | 4/1986 | Bergeret et al. | 525/333.4 |

OTHER PUBLICATIONS

Clerici et al., "Internal Metallation of N- or P-Donor Bidentate Lignads to Give Multidentate Organometallic Compounds", J. Chem. Commun., 1973, 516–517.
Sommer, "Zur Spaltung Tertiarer Phosphine. I", Z. Anorg. Allg. Chem., vol. 36, 1970, 37–43.
Moedritzer et al., "Synthesis and Properties of Mono- and Poly- Methylene-Diphosphonic Acids and Esters", J. Inory Nucl., Chem., vol. 22, 1961, 297–304.
Kosolapoff & Maier, "Organic Phosphorus Compounds", Wiley Interscience, vol. 1, 32–35, 41–47, 343–360.
Hays, "The Reaction of Diethyl Phosphonate with Methyl and Ethyl Grignard Reagents", J. Org. Chem., vol. 33, No. 10, Oct. 1968, 3690–3694.
Kosolapoff et al., "Diphosphine Dioxides. Part II. Some Diphosphine Dioxides with Mono-, Di-, Tri-Methylene Bridges." J., 1961, 2423–2427.
Tsvetkov et al., "A Simple Synthesis and Some Synthetic Applications of Substituted Phosphide and Phosphite Anions.", Synthesis 1986, 198–208.
Kosolapoff et al., "Some Aliphatic Diphosphonic Tetrachlorides. Part II. Some Reactions of Diphosphonic Tetrachlorides", J. Chem. Soc., 1967, 1789–1791.
Clarke et al., "Synthesis and Physical Properties of Chlorodi (o-Tolyl) Phosphine, Lithium Di(o-Tolyl) Phosphide and Diphosphine Series (o-Tolyl)$_2$P(CH$_2$)$_n$P(o-Tolyl)", J. Organometal. Chem., 1981 51–59.

Primary Examiner—Anton H. Sutto
Attorney, Agent, or Firm—Reynold J. Finnegan

[57] ABSTRACT

A process for the production of organic bisphosphine dioxides from organic bisphosphonates. The organic bisphosphonate is reacted with a Grignard reagent to give relatively high yields of the organic bisphosphine dioxide.

15 Claims, No Drawings

BISPHOSPHINE DIOXIDES

The Government of the United States of America has rights in this invention pursuant to Contract No. DE-AC22-84PC70022 awarded by the U.S. Department of Energy.

FIELD OF INVENTION

This invention relates to a novel method for the production of organic bisphosphine dioxides at relatively high yield and to certain novel organic bisphosphine dioxides.

DESCRIPTION OF THE PRIOR ART

The production of bisphosphine dioxides has been carried out by many procedures. In U.K. Application No. GB 2,101,601A, filed by G. Dyer et. al., and published Jan. 19, 1981, there is disclosed a method involving preparation of a bisphosphonium salt followed by hydrolysis to the bisphosphine dioxides as discussed on pages 1 to 6 of the British specification. The bisphosphine dioxides are then reduced to the bisphosphines. Nowhere in this reference is there any disclosure of Grignard reagents or their use in the Process.

In U.S. Pat. No. 3,532,774, issued on Oct. 6, 1970 to L. Maier, bisphosphine dioxides are produced by heating an aminophosphine with a dihydroxyl compound to form a bisphosphonite which is then isomerized to its bisphosphine dioxide. This is not the process of this patent application.

In U.S. Pat. No. 4,447,584, issued on May 8, 1984 to W. Bergeret et al. (and U.S. Pat. No. 4,581,416 the division thereof issued on Apr. 8, 1986), a two step process is disclosed capable of producing bisphosphine dioxides. In the disclosed process a secondary phosphine oxide of the formula

is reacted in the first step with an alkali metal amide (which can optionally be activated) to form the alkali metal phosphinite of the formula

in which M is the alkali metal. The alkali metal phosphinite is reacted in the second step with a dihalogen compound to yield the bisphosphine dioxide, as shown in Examples 3 to 7, 26 to 30, 32, and 33 of the patents. The process is not the process of the instant patent application in which the starting material is an organic bisphosphonate.

In a paper entitled "A Simple Synthesis and Some Synthetic Applications of Substituted Phosphide and Phosphinite Anions" by E. N. Tsvetkov et al., Synthesis 1986, 198–208, a wide variety of phosphorus compounds were Prepared using concentrated aqueous alkali solutions. Bisphosphine dioxides were prepared by the procedure of Scheme I on pages 203, 204 and 207, with the results summarized in Table 8. The process involved the reaction of a phosphinous acid with a dihaloalkane using a concentrated aqueous solution of an alkali metal hydroxide. This is not the process of this patent application.

A paper by G. M. Kosolapoff et al., "Some Aliphatic Disphoshonic Tetrachlorides. Part II. Some Reactions of Diphosphonic Tetrachlorides", J. Chem. Soc., 1967, 1789–1791, discusses the formation of bisphosphine dioxides. The process employed in this article is the reaction of a diphosphinic tetrachloride of the structure:

with a Grignard reagent to form the corresponding bisphosphine dioxide, as was disclosed in the second column on page 1789 and the first column on page 1791. There is no disclosure or suggestion that one could react a Grignard reagent with a halogen-free bisdiphosphonate to obtain the bisphosphine dioxide.

In the article "Synthesis and Physical Properties of Chlorodi(o-Tolyl)Phosphine, Lithium Di(o-Tolyl)-Phosphide and Diphosphine Series (o-Tolyl)$_2$P(CH$_2$)$_n$-P(o-Tolyl) (n=1–4, 6, 8)", P. W. Clark et. al. J. Organometal. Chem., 1981, 51–59, the Grignard reagent o-tolyl magnesium chloride was reacted with phosphorus trichloride to form chloridi-o-tolylphosphine. This was then reacted with lithium in anhydrous solvent to obtain a solution of lithium di-o-tolylphosphide which was reacted with an aliphatic dihaloalkane to yield the corresponding bisphosphine. Though a Grignard reaction is used, the process or sequence of reactions is not the reaction claimed in this patent application.

In the first column on page 17 (lines 5 to 7 of the new paragraph) M. G. Clerici et al., in their article "Internal Metallation of N- or P-Donor Bidentate Ligands to Give Multidentate Organometallic Compounds", J. Chem. Soc., Chem. Commun., 1973, 516-517, the authors disclose the production of the bisphosphine (o-tolyl)$_2$-P(CH$_2$)$_n$P(o-tolyl)$_2$ from (o-tolyl)$_2$PLi and dichloroethane or dibromoethane. However, they show nothing pertaining to bisphosphine dioxides or the use of Grignard reagents.

Another procedure for producing bisphosphines is shown in "Zur Spaltung tertiarer. Phosphine I", K. Sommer, Z. Anorg. Allg. Chem., Vol. 36, 1970, 37–43. This process involves the reaction of a metal organic phosphide, e.g., lithium diphenylphosphide, with a dihaloalkane, e.g., dichloroethane to form an organic bisphosphine (p. 37).

The organic bisphosphonates have long been known as shown by K. Moedritzer et al., "Synthesis and Properties of Mono- and Poly-Methylene-Diphosphonic Acids and Esters", J. Inorg. Nucl. Chem., Vol. 22, 1961, 297–304. This reference, however, does not show the conversion of these organic bisphosphonates to their corresponding organic bisphosphine dioxides.

Chapters 1 and 2 of "Organic Phosphorus Compounds", G. M. Kosolapoff and L. Maier, Wiley Interscience, N.Y., Vol. 1, discuss many of the reactions phosphorus compounds will undergo and methods for the preparation of various phosphorus compounds. However, nowhere is there any suggestion or disclosure that organic bisphosphonates will react with Grignard reagents to produce the corresponding organic bisphosphine dioxides in high yield. In pages 32 to 35 of this reference the reaction of Grignard reagents with phosphorus halides to form tertiary phosphines is discussed. In this reaction the halogen atom (—X) attached to the phosphorus atom (P—X) is cleaved and replaced by the organic group of the Grignard reagent. This differs from the process of this invention in which a metathesis reaction occurs and the alkoxy group (RO—) attached to the phosphorus atom (P—OR) is replaced; this metathesis reaction is not discussed or suggested for this reaction. On pages 41 to 47 of this reference there are disclosed other methods for the production of phosphines by the reaction of alkali metal phosphides with alkylating agents such as the alkyl halides, and by the reduction of tertiary phosphine dioxides with, for example, trichlorosilane or other reducing agents. On pages 343 to 360 several methods of Preparing phosphine dioxides are disclosed; however, none of these methods suggest their preparation by the metathesis of phosphonates with Grignard reagents. One of the methods disclosed (pages 343 to 349) is the oxidation of the phosphine to the corresponding phosphine oxide with a wide variety of oxidants. It is reported that under some air oxidation reactions a mixture of phosphine dioxides and phosphinate esters can result. Another method (pages 349 to 354) involves the decomposition of phosphonium hydroxides by various techniques. On pages 354 to 357 the preparation of phosphine dioxides by the reaction of a phosphorus oxyhalide with a Grignard reagent is shown. This reaction relies on the presence of a halogen atom in the phosphorus compound that will be capable of reacting with the Grignard reagent. On pages 357 to 359 the preparation of tertiary phosphine dioxides from triarylphosphates and Grignard reagents is reported to result in generally low yields. Many reactions are discussed concerning the formation of the monophosphine dioxides and are illustrated by general equations and formulas. The sole mention of bridged diphosphine dioxides is found in the brief phrase "bridged diphosphine dioxides" on the third line from the bottom on page 358, with reference to footnotes No. 327 and No. 484.

The paper referred to as footnote No. 327 is an article by H. R. Hays entitled "The Reaction of Diethyl Phosphonate with Methyl and Ethyl Grignard Reagents", J. Org. Chem., Vol 33, No. 10, October, 1968, pages 3690 to 3694. This article discusses the production of numerous monophosphine oxides from phosphonates reacted with Grignard reagents but nowhere discloses the use of this reaction to produce bisphosphine dioxides. The sole mention of bisphosphine dioxides is in the first column, last paragraph, on page 3693 and the second column, first full paragraph on page 3694, wherein the preparation of 1,2-bis(dimethylphosphinyl)butane (or alkane) is described. The process disclosed there involves the alkylation of the intermediate phosphine oxide of Formula II in the reference, R$_2$POMgX, with a 1,2-dichloroalkane, e.g., 1,2-dichlorobutane. This is not our claimed Process for producing biphosphine dioxides, the process Produces biphosphines.

The paper referred to as footnote No. 484 is an article by G. M. Kosolapoff and R. F. Struck entitled "Diphosphine Dioxides. Part II. Some Diphosphine Dioxides with Mono-, Di-, and Tri-methylene Bridges" J., 1961, pages 2423 to 2427. This article discusses various routes for the preparation of bisphosphine dioxides. In the Experimental section on pages 2426 bisphosphine dioxides were produced by the reaction of an alkylene di-toluene-p-sulfonate with a Grignard reagent and diethyl hydrogen phosphonate. This procedure was used to prepare tetra-P-butyl-tri-methylenediphosphine dioxide in 43% yield. The authors then noted "Only a trace of this material was formed after a 24-hour reaction of an excess of butylmagnesium bromide and tetraethyl trimethylene-diphosphonate in boiling dipentyl ether". This statement is a positive and clear pronouncement by the authors that this process was not an acceptable means for producing organic bisphosphine dioxides from organic bisphosphonates.

SUMMARY OF THE INVENTION

The process of this invention is based on the discovery that organic bisphosphonates can be reacted with Grignard reagents to produce organic bishosphine dioxides at relatively high yield.

DETAILED DESCRIPTION OF THE INVENTION

Though the preparation and properties of bisphosphine dioxides, such as 1,3-bis(diphenylphosphine oxide)propane, have been reported, as discussed in the Prior Art section, to the best of our knowledge none of the prior art suggests or discloses the process for their production that is the subject of this invention. Despite the numerous procedures described in the prior art, none of the disclosures indicate that the organic bisphosphonates hereinafter identified by Formula II will react with a Grignard reagent to produce the organic bisphosphine dioxides hereinafter identified by Formula I in relatively high yield. That this could be accomplished was an unexpected and unpredictable finding, particularly in view of the findings reported by G. M. Kosolapoff and R. F. Struck on page 2426 of their article in J., 1961. In this article, as mentioned supra in the "Description of the Prior Art" section of this application, they mention their attempted reaction of the Grignard reagent butylmagnesium bromide and tetraethyl trimethylenediphosphonate (also known as 1,3-bis(diethylphosphonate)propane). They report formation of only a trace of tetra-P-butyltrimethylphosphine dioxide (also known as 1,3-bis(diethylphosphine oxide)propane) after a 24 hour reaction at reflux. Thus, the fact that the instant inventor was able to carry out his claimed invention and obtain relatively high yields of organic bisphosphine dioxides from organic bisphosphonates was completely unexpected and unpredictable and no reason can be submitted to explain why applicant was able to do so whereas the authors of the publication were not.

The present invention is based on the unexpected and unpredictable discovery of a process whereby organic bisphosphonate compounds that do not contain a halogen atom can be reacted with excess Grignard reagent to produce organic bisphosphine dioxides.

The organic bisphosphine dioxides produced are represented by the general formula:

wherein Z is a linear or branched divalent alkylene group or alkenylene group having from 1 to about 10 carbon atoms, preferably 2 to about 6 carbon atoms, and most preferably 3 carbon atoms, or Z can be a divalent cyclic bridging group having from 4 to about 10 ring carbon atoms, e.g., cyclobutylene, cyclpentylene, cyclohexylene, cycloheptylene, phenylene, tolylene, naphthylene, the Z group can be unsubstituted or substituted as discussed infra in the definitions of the organic bisphosphonate compounds; and R' is a linear or branched alkyl group having from 1 to about 10 carbon atoms, preferably from 2 to about 5 carbon atoms, or an aryl, aralkyl or alkaryl group having 6 or 10 carbon atoms in the aryl moiety (phenyl, naphthyl) and from 1 to about 10 carbon atoms, preferably from 1 to about 3 carbon atoms, in the alk-moiety. The R' radicals can be the same or different.

Illustrative of organic bisphosphine dioxides of Formula I that can be produced by the process of this invention one can mention:

a: bis(diphenylphosphine oxide)methane,
b: 1,3-bis(diphenylphosphine oxide)propane,
c: 1,10-bis(diphenylphosphine oxide)decane,
d: 1,3-bis(diethylphosphine oxide)propane,
e: 1,3-bis(ethyl phenylphosphine oxide)propane,
f: 1,4-bis(diphenylphosphine oxide)butane,
g: 1,3-bis(dipropylphosphine oxide)propane,
h: 1-diethylphosphine oxide-3-dipropylphosphine oxide propane,
i: 1-diethylphosphine oxide-3-diphenylphosphine oxide propane,
j: 1,3-bis(diphenylphosphine oxide)-2-methylpropane,
k: 1,3-bis(diphenylphosphine oxide)-1-butylpropane,
l: 1-diamylphosphine oxide-3-diphenyl-phosphine oxide-1,3-diethylpropane,
m: 1,3-bis(diphenylphosphine oxide)-2,2-dimethylpropane,
n: 1,2-bis(diphenylphosphine oxide)propane,
o: 1,2-bis(diphenylphosphine oxide)benzene,
p: 1,4-bis(diphenylphosphine oxide)cyclohexane, and the like.

In the process for producing the organic bisphosphine dioxides of Formula I an organic bisphosphonate II is reacted with a Grignard reagent.

A wide variety of organic bisphosphine dioxides of Formula I can be produced from the same organic bisphosphonate of Formula II by selection of the proper Grignard reagent. This results from the fact that in the metathesis reaction the organic group present in the Grignard reagent displaces the alkoxy group attached to the phosphorus atom of the organic bisphosphonate and regardless of what the alkoxy group is the R' group in Formula I will be the organic R' group that was present in the Grignard reagent. For instance, starting with 1,3-bis(diethylphosphonate)propane and reacting it with phenyl magnesium bromide will yield, 1,3-bis(diphenylphosphine oxide)propane; but reacting it with propyl magnesium bromide will yield, 1,3-bis(dipropylphosphine oxide)propane.

The organic bisphosphonates that can be used in the process are represented by the general formula:

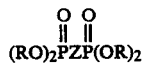   (II)

wherein Z is previously defined and R is the same as previously defined for R'. It is to be noted that Z can be unsubstituted or it can be substituted with groups that do not have a significant adverse effect on the reaction of the organic bisphosphonate compound with the Grignard reagent. These compounds and the methods for their preparation are known to those skilled in the art, the literature containing many disclosures of various methods for their preparation.

In an exemplary procedure, 1,3-bis(diethylphosphonate)propane is Prepared under an inert gas atmosphere and anhydrous conditions by the reaction of diethylphosphite, sodium and 1,3-dibromopropane in ether, a procedure well known to these of ordinary skill in the art, under published conditions. Similarly any of the known organic phosphites can be reacted, alone or as mixtures, to produce the organic bisphosphonates.

The organic phosphites are represented by the general formula:

wherein R has the same meaning previously defined. The alkali metal or alkaline earth metal salts of these compounds are reacted with a dihalogenated organic compound of the general formula XZX (e.g., 1,3-dibromopropane) to form the organic bisphosphonate. In this formula Z has the meanings previously defined and X is a halogen atom, e.g., chlorine, bromine, iodine.

Illustrative of organic phosphites that can be used one can mention diethylphosphite, diphenylphosphite, ethyl phenylphosphite, dipropylphosphite, diamylphosphite, dihexylphosphite, dicyclohexylphosphite, ditolylphosphite, diphenethylphosphite, di-2-ethylhexylphosphite, dinaphthylphosphite, and the like.

Illustrative of dihalogenated organic compounds one can mention dichloromethane, dibromomethane, diiodoethane, dibromoethane, diiodoethane, chlorobromoethane, 1,2-dibromopropane, 1,3-dibromopropane, 1,4-dichlorobutane, 1,4-dibromobutane, 1,2-dibromobenzene, 1,4-dibromocyclohexane, 1,4-dibromo-2-methylbenzene, 1,10-dibromodecane, and the like.

Illustrative of organic bisphosphonates of Formula II are the corresponding phosphonates of the organic bisphosphine dioxides (a) to (p) previously identified. For example, 1,3-bis(diphenylphosphonate)propane is the corresponding Phosphonate of organic bisdiphosphine dioxide (b) above, namely, 1,3-bis(diphenylphosphine oxide)propane.

In producing the organic bisphosphine dioxides of Formula I one reacts an organic bisphosphonate of Formula II with excess Grignard reagent. The preparation of the latter compounds and their chemical structures have long been known. In the reaction from at least 1 to about 6 or more, say 20, molar equivalents of the Grignard reagent per molar equivalent of organic bisphosphonate is used.

In regard to the Grignard reagents, Kirk-Othmer, Encyclopedia of Chemical Technology, Interscience Publishers, Inc., New York, N.Y., U.S.A., 1951, Volume 7, pages 314–324, discloses the preparation of Grignard reagents. These well known compounds are represented by the general formula:

(III) R'MX 

wherein X is a halogen atom (chlorine, fluorine, bromine, iodine), M is a metal (Mg, Zn, Al) and R' is an alkyl, aryl, alkaryl or aralkyl group as herein before defined free of substituent groups known to deleteriously affect the preparation of the Grignard compounds. These reagents are essentially alkyl- or aryl-metal halides, prepared by the addition of an organic halohydrocarbon to the metal turnings, generally in the presence of an ether. The methods for their preparation are so well known and readily available that there is no need for further discussion here. Further, many of them are commercially available for laboratory and commercial use. In a typical preparation an ethereal solution of the selected organic halide is added to a stirred suspension of magnesium turnings in anhydrous ether. The reaction is carried out under anhydrous conditions and in the absence of oxygen since both moisture and oxygen react with Grignard reagents. As is known,, an equilibrium exists in the solution

Illustrative Grignard reagents are phenyl magnesium bromide, phenyl magnesium chloride, ethyl magnesium bromide, propyl magnesium bromide, amyl magnesium bromide, tolyl magnesium bromide, phenethyl magnesium bromide, and the like, as well as their corresponding other halides, and the corresponding zinc and aluminium compounds.

The organic bisphosphine dioxides I can be used to produce organic bisdiphosphines of the general formula:

wherein R and Z have the meanings hereinbefore defined, by known methods, e.g., as described in the article by L. D. Quin et al., J. Am. Chem. Soc., 1984, 106, 7021–7032. In a typical reaction the bisdiphosphine dioxide of Formula I is reduced, e.g., with trichlorosilane, to its corresponding bisdiphosphine of Formula V.

Illustrative organic bisdiphosphines of Formula V are bisdiphenylphosphinemethane, 1,2-bisdiphenylphosphine-ethane, 1,3-bisdiphenylphosphinepropane, 1,10-bisdiphenylphosphinedecane, 1,3-bisdiethylphosphinepropane, 1,3-bisethylphenylphosphine-propane, 1,4-bisdiphenylphosphinebutane, 1,3-bisdipropylphosphinepropane, 1-diethyl-phosphine-3-dipropylphophinepropane, 1-diethylphosphine-3-dipropylphosphinepropane, 1,3-bisdiphenylphosphine-2-methylpropane, 1,3-bisdiphenyl-phosphine-1-butylpropane, 1-diamylphosphine-3-diphenylphosphine-1,3-diethylpropane, 1,3-bisdiphenylphosphine-2,2-dimethylpropane, 1,2-bisdiphenylphosphinepropane, 1,2-bisdiphenylphosphenebenzene, 1,4-bisdiphenyl-phosphinecyclohexane, and the like.

In a typical reaction for the production of the organic bisphosphines, diethylphosphite is reacted with 1,3-dibromopropane to produce 1,3-bis(diethylphosphonate)propane. The 1,3-bis(diethylphosphonate)propane is reacted with phenyl magnesium bromide and converted to 1,3-bis(diphenylphosphine oxide)propane, which is in turn reduced to 1,3-bis(diphenylphosphine)-propane.

The bisdiphosphorus compounds of general Formulas I, II and V can be used as ligands in conjunction with known metal-based catalysts, e.g., catalysts containing the metals cobalt, rhodium, ruthenium, palladium, osmium, iridium, platinum, rhenium, nickel, etc., in catalytic reactions employing synthesis gas to produce organic compounds by homologation and carbonylation reactions. These processes for the manufacture of organic compounds from synthesis gas are well known and fully described in the literature. Generally the processes employ promoters (e.g., iodine), co-catalysts, and co-ligands, and can be heterogeneous or homogeneous reactions. The compounds of Formulas I, II and V are generally excellent ligands and/or promoters for the metal-catalyzed conversion of methanol to higher organic oxygenates when reacted with carbon monoxide or synthesis gas.

The reaction of the organic bisphosphonates of Formula II with the Grignard reagent III to produce the organic bisphosphine dioxides of Formula I is carried out under an inert atmosphere under essentially anhydrous conditions due to the high reactivity of the Grignard reagents with water. Pressure is not critical, nor is temperature. However, a suitable temperature is required for the reaction to proceed and will vary according to the starting materials employed. Any temperature up to the reflux temperature of the reaction mixture can be employed. Normally a slight excess of Grignard reagent is used to enhance essentially complete conversion of the bisphosphonate II to the bisphosphine dioxide I. Reaction time will vary depending upon the size of the batch. Any suitable solvent, e.g., tetrahydrofuran, ether, benzene, etc., or mixture of solvents can be used. As is known the solvent can have an effect on conversion and yield, therefore, some preliminary routine experimentation may be necessary before arriving at the best solvent in a particular reaction.

Illustrative of the method for producing the starting organic bisphosphonates is the procedure shown in Experiment A.

EXPERIMENT A

A dry one liter reaction flask equipped with a condenser, nitrogen inlet tube, magnetic stirrer and addition funnel was charged with 17.66 g of sodium under dry, nitrogen Purged conditions and 200 mL of dry anhydrous diethyl ether was added. Placed 99 mL of dry diethylphosphite and 100 mL of dry diethyl ether in the addition funnel and this solution was slowly dripped into the reaction flask that was kept immersed in an ice bath. Hydrogen evolution was monitored with a bubbler. In about one hour a white solid started to form. The reaction mixture was stirred overnight at room temperature and then 39 mL of dry 1,3-dibromopropane was added via the funnel at a fast drip. In about 15 minutes the exothermic reaction reached reflux. After about 40 minutes heat was applied to continue refluxing for a total of 4 hours. The mixture was cooled to room temperature and the slurry was filtered and washed with dry ether under nitrogen. The filtrate was stripped overnight under vacuum and 106 g of 1,3-bis(diethylphosphonate)propane was recovered.

The following examples serve to further illustrate the invention. Parts are by weight, unless otherwise indicated.

EXAMPLE 1

A 100 mL reaction flask was equipped with a septum sealed pressure equalizing addition funnel, dry ice condenser, nitrogen inlet tube, thermometer and magnetic stirrer and flushed well with dry nitrogen. In a glove box there were added to the flask 25 mL of dry tetrahydrofuran and 1.73 g of 1,3-bis(diethylphosphonate)propane (0.00547 m) by means of syringes. After removal from the glove box a 9.5 mL portion of a 3 molar solution of phenyl magnesium bromide (0.0284 m) in diethyl ether was syringed into the addition funnel and then added dropwise to the reaction flask. The temperature increased from 22° C. to 34° C. and the mixture became cloudy. It was refluxed for seven hours and then stirred at room temperature over the weekend. Reflux was resumed and ether was removed; reflux was continued for 7.5 hours at about 67° C. After cooling 20 mL of 0.1 N hydrochloric acid was added followed by 20 mL of toluene and 30 mL of dilute sulfuric acid. The emulsion separated into an organic top yellow layer and as aqueous bottom colorless layer. The aqueous layer was removed and washed with toluene, the wash being added to the original organic layer. The organic layer was vacuum stripped leaving a gummy pale yellow residue of 1,3-bis(diphenylphosphine oxide)propane, whose structure was confirmed by NMR comparison with an authentic sample of this compound.

EXAMPLE 2

Using the equipment described in Example 1 and essentially the same procedure 10 g of 1,3-bis(diethylphosphonate)propane (0.03162 m) was reacted with 55 mL of the phenyl magnesium bromide solution (0.165 m). The reaction mixture was stirred at reflux for 7 hours, at room temperature overnight and then another 7 hours at reflux. It was cooled to about 30° C., 125 mL of 0.5 N hydrochloric acid and 70 mL toluene were added. The layers were separated and the aqueous layer extracted three times with 100 mL portions of toluene. The toluene fractions were added to the original organic layer which was then dried over magnesium sulfate, filtered, and the toluene removed under vacuum to yield 10.8 g of gummy, yellow solid 1,3-bis(diphenylphosphine oxide)propane. This was slurried in 50 mL of dry pentane, filtered, reslurried in 20 mL dry heptane, filtered, and dried.

EXAMPLE 3

In a glove box 4.4 g of activated magnesium was added to a flask equipped with a condenser, nitrogen inlet tube, addition funnel and magnetic stirrer. The magnesium had been activated by briskly stirring turnings in a reactor under a nitrogen atmosphere overnight. The equipment was removed from the glove box and 75 mL of dry tetrahydrofuran was syringed into the reaction flask. A 28.12 g portion of 4-bromotoluene, which had been distilled from phosphorus pentoxide and stored under nitrogen, and 25 mL of dry tetrahydrofuran were placed into the addition funnel. This solution was slowly added in a dropwise manner to the reaction flask. It was necessary to warm the flask in a water bath during the early part of the addition to start the reaction, once started the bath was removed. The mixture was refluxed for two hours and cooled to room temperature at which point a thick slurry of tolyl magnesium bromide formed. The p-tolyl magnesium bromide mixture was transferred, with slight warming, via cannula to the addition funnel atop a 500 mL flask, equipped as described in Example 1, that contained 10 g (0.0316 m) of 1,3-bis(diethylphosphonate)propane and 90 mL of dry tetrahydrofuran, and then added in a dropwise manner from the funnel into the flask. An exothermic reaction occurred and after all of the Grignard reagent had been added the reaction mixture was refluxed for 15 hours. The mixture was cooled, 12.5 mL of 1 N hydrochloric acid was added, stirred for 3 hours at room temperature, and allowed to stand to separate the layers. The aqueous layer was removed and washed with three 100 mL portions of diethyl ether. The ether washes were added to the organic layer which was then dried over magnesium sulfate, filtered, and the solvents removed under vacuum. There was recovered 11.47 g of 1,3-bis(di-p-tolyphosphine oxide) propane; 70% yield.

EXAMPLE 4

A 500 mL reaction flask equipped with a thermometer, pressure equalizing addition funnel, gas inlet tube and reflux condenser was dried, flushed with nitrogen and then 200 mL of one molar p-chlorophenyl magnesium bromide was added. Next about 40 mL of dry tetrahydrofuran and 12.8 g (0.04 m) of 1,3-bis(diethylphosphonate)propane were placed in the addition funnel and this solution was added dropwise, with stirring, to the Grignard reagent over about a 12 minute period. Some solid formed and the reaction exothermed to about 33° C. The addition funnel was washed with 40 mL of dry tetrahydrofuran, which was added to the reaction flask Much of the solid dissolved when the tetrahydrofuran was added; the mixture was stirred at room temperature for 30 minutes and then refluxed for a total of about 60 hours. The yellowish mixture was cooled in an ice water bath and 170 mL of 1.5 N hydrochloric acid was added. The pH was 9-10 and the mixture was still an emulsion. Concentrated hydrochloric acid was added to lower the pH to 6-7 to break the emulsion. After stirring for 3 hours the mixture was let stand to separate layers. The aqueous layer was removed and washed with three 100 mL portions of diethyl ether. The ether washes were added to the organic layer which was then dried over magnesium sulfate, filtered, and the solvents removed under vacuum. There was recovered 18.02 g of 1,3-bis(di-p-chlorophenylphosphine oxide)propane; 76% yield.

EXAMPLE 5

Following the procedure described in Example 3, p-tolyl magnesium bromide was produced in a one liter reaction flask from 8.8 g activated magnesium, 46.8 mL 4-bromotoluene and 150 mL dry tetrahydrofuran. This Grignard reagent was then cooled in an ice bath and a mixture of 17.3 mL of 1,3-bis(diethylphosphonate)propane and 110 mL of dry tetrahydrofuran was added at a moderate dropwise rate. The reaction was stirred at reflux for 15 hours and cooled. While stirring and cooling in an ice bath 200 ml of 1.5 molar by hydrochloric acid and 25 ml of 6 molar hydrochloric acid were added to the slurry to lower the pH to about 6-7, at which the precipitate dissolved and two layers formed. The aqueous layer was removed and washed with four 100 mL portions of diethyl ether. The ether washes were added to the organic layer which was then dried over magnesium sulfate, filtered, and the solvents removed using a rotovaporator. There was recovered 10.3 g of 1,3-bis(-di-p-tolylphosphine oxide)propane as an oil, having about 90% purity. Extraction of the magnesium sulfate dessicant with toluene recovered an additional 0.9 g of the product.

EXAMPLE 6

Using essentially the same procedure and equipment described in Example 5, p-tolymagnesium bromide Grignard reagent was produced from 9.83 g of magnesium in 200 mL of dry tetrahydrofuran and 68.77 g of 4-bromotoluene in 75 mL of dry tetrahydrofuran. In a slow dropwise manner a solution of 25 g of 1,3-bis(diethylphosphonate)propane in 25 mL of dry tetrahydrofuran was added to the Grignard reagent via the addition funnel. The funnel was then rinsed into the flask with 25 mL of dry tetrahydrofuran and the reaction mixture in the flask was refluxed for a total of about 30 hours. A 1.2 molar hydrochloric acid solution was added to lower the pH to 9; this was followed by concentrated hydrochloric acid to a pH of 2. The mixture was stirred 3 hours and let sit overnight. The aqueous layer was removed and washed with four 100 ml portion of diethyl ether. The ether washes were added to the organic layer and the mixture stripped on a rotovaporator. The residue was taken up into a tetrahydrofuran-ether mixture and extracted with saturated aqueous ammonium chloride. The layers were separated and the organic layer was stripped to remove solvents. The yield of 1,3-bis(di-p-tolylphosphine oxide)propane was 28.4 g; 72% yield.

EXAMPLE 7

Using essentially the equipment described in Example 4, 220 mL of o-tolylmagnesium chloride was added to the reactor. To the funnel there were syringed 25 g of 1,3-bis(diethylphosphonate)propane and 25 mL of dry tetrahydrofuran. This solution was added to the contents of the reactor in a dropwise manner while stirring; no temperature increase was noted. The reaction mixture was stirred at reflux for a total of 58 hours and cooled. To the dark organge-brown solution 75 mL of 1.5 N hydrochloric acid was slowly added. The mixture exothermed to 70° C. Then about 30 mL of concentrated hydrochloric acid was added to a pH of 3, the mixture was stirred for 2.5 hours and then left standing to separate the layers. The organic yellow layer was recovered. The aqueous layer was extracted with four 100 mL portions of diethyl ether and these were added to the organic layer. The organics were washed with saturated ammonium chloride, separated, stripped on a rotovaporator and dried overnight at room temperature under vacuum. The solids were dissolved in the minimum amount of hot tetrahydrofuran required and placed in the refrigerator for a total of 48 hours. A slight white precipitate was filtered and discarded. Solvents in the filtrate were evaporated at room temperature under vacuum. The residual yield of 1,3-bis(di-o-tolylphosphine oxide)propane was 31.3 g; 78.5% yield.

What is claimed is:

1. A process for the production of an organic bisphosphine oxide of the general formula:

 (I)

which consists of reacting an organize bisphosphonate of the general formula:

 (II)

under essentially anhydrous conditions with from at least one to about six molar equivalents of a reagent of the general formula:

R'MX (III)

and recovering said organic bisphosphine oxide; wherein R is an alkyl group having from 1 to about 10 carbon atoms; R' is an aryl or aralkyl or alkaryl group having 6 to 10 ring carbon atoms in the aryl-moiety and from 1 to about 10 carbon atoms in the alk-moiety; Z is a divalent alkylene or alkenylene group having from 1 to about 10 carbon atoms, or a divalent cyclic bridging group having from 4 to about 10 ring carbon atoms; M is a metal atom from the group consisting of Mg or Zn or Al; and X is a halogen atom.

2. A process as defined in claim 1 wherein R is an alkyl group having from 2 to 5 carbon atoms.

3. A process as claimed in claim 1, wherein the alk-moiety has from 1 to 3 carbon atoms.

4. A process as claimed in claim 1, wherein R' in Formulas I and III is phenyl.

5. A process as claimed in claim 1, wherein R' is Formulas I and III is p-tolyl.

6. A process as claimed in claim 1, wherein R' in Formulas I and III is o-tolyl.

7. A process as claimed in claim 1, wherein R' in Formulas I and III is chlorophenyl.

8. A process is claimed in claim 1, wherein Z is divalent —CH$_2$CH$_2$CH$_2$—.

9. A process as claimed in claim 1, wherein Z is a divalent alkylene or alkenylene group having from 2 to 6 carbon atoms.

10. A process as claimed in claim 1, wherein M is magnesium.

11. A process as defined in claim 1, wherein R in Formula II is ethyl.

12. A process as claimed in claim 1, wherein Formula I compound is 1,3-bis(diphenylphosphine oxide)propane, Formula II compound is 1,3-bis(diethylphosphonate)propane and Formula III compound is phenyl magnesium bromide.

13. A process as claimed in claim 1, wherein Formula I compound is 1,3-bis(diphenylphosphine oxide)propane, Formula II compound is 1,3-bis(diethylphosphonate)propane and Formula III compound is p-tolyl magnesium bromide.

14. A process as claimed in claim 1, wherein Formula I compound is 1,3-bis(di-p-chlorophenylphosphine oxide)propane, Formula II compound is 1,3-bis(diethylphosphonate)propane and Formula III compound is p-chlorophenyl magnesium bromide.

15. A process as claimed in claim 1, wherein formula I compound is 1,3-bis(di-o-tolylphosphine oxide)propane, Formula II compound is 1,3-bis(diethylphosphonate)propane and Formula III compound is o-tolyl magnesium chloride.

* * * * *